United States Patent [19]

McQuigg et al.

[11] Patent Number: 5,180,822
[45] Date of Patent: Jan. 19, 1993

[54] HIGHLY SELECTIVE CHELATING RESINS AND MONOMERS FOR THEIR PREPARATION

[75] Inventors: Donald W. McQuigg; Edward E. Sowers, both of Mooresville, Ind.

[73] Assignee: Reilly Industries, Inc., Indianapolis, Ind.

[21] Appl. No.: 750,467

[22] Filed: Aug. 27, 1991

Related U.S. Application Data

[60] Continuation-in-part of Ser. No. 609,393, Nov. 5, 1990, Pat. No. 5,147,954, which is a division of Ser. No. 352,980, May 17, 1989, Pat. No. 4,968,806, which is a continuation-in-part of Ser. No. 247,152, Sep. 21, 1988, Pat. No. 5,015,706.

[51] Int. Cl.$^5$ ............... C07D 401/00; C07D 213/36; C07D 211/70
[52] U.S. Cl. ............................. 546/278; 546/264; 546/329
[58] Field of Search .................. 546/329, 264, 278

[56] References Cited

U.S. PATENT DOCUMENTS 4,031,038  6/1977  Grinstead et al. .............. 620/2.2
4,202,944  5/1980  Hancock et al. ................ 521/32
4,533,621  8/1985  Ikeuchi et al. ................. 430/213

OTHER PUBLICATIONS

Montheard, Jean-Pierre, et al., "Chemical Transformations of Chloromethylated Polystyrene," *J. Macromol. Sci.-Rev.*, Macromol. Chem Phys., C28(3&4), 503-592 (1988).

Camps, Marcel, et al., "Chloromethylstyrene: Synthesis, Polymerization, Transformations, Applications," *J. Macromol. Sci.-Rev.*, Macromol. Chem Phys., C22(3), 343-407 (1982-83).

Tomoi, Masao, et al., "Synthesis and Catalytic Activity of Polymer-Bound 4-(N-Benzyl-N-methylamino)-pyridine," *Macromol. Chem.*, Rapid Commun. 3. 537-542 (1982).

Primary Examiner—Joseph L. Schofer
Assistant Examiner—Alex H. Walker
Attorney, Agent, or Firm—Woodard, Emhardt, Naughton, Moriarty & McNett

[57] ABSTRACT

Described are preferred monomers including a vinylbenzyl moiety N-bonded to an alkylaminopyridinyl or pyridylimidazolyl function. Also described are preferred acid salts of such monomers. Additionally, preferred processes involving and resins formed from these preferred monomers are described. The preferred resins are highly selective for valuable heavy metal ions such as copper and demonstrate superior iron rejection values.

22 Claims, No Drawings

HIGHLY SELECTIVE CHELATING RESINS AND MONOMERS FOR THEIR PREPARATION

CROSS REFERENCE TO RELATED APPLICATIONS

This is a continuation-in-part of U.S. application Ser. No. 609,393 filed Nov. 5, 1990, now U.S. Pat. No. 5,147,954, which is a divisional of U.S. patent application Ser. No. 352,980 filed May 17, 1989, now issued U.S. Pat. No. 4,968,806 which is hereby incorporated herein by reference in its entirety, which is a continuation-in-part of U.S. patent application Ser. No. 247,152 filed Sep. 21, 1988, now issued U.S. Pat. No. 5,015,706.

BACKGROUND OF THE INVENTION

The instant invention relates generally to chelating resins, and in particular to highly selective chelating resins having alkylaminopyridyl or pyridylimidazolyl functions, and to monomers for their preparation.

As background, polymer resins having ion-exchange properties have long been used to recover metal ions from solution. This recovery technique is advantageous because the resin insolubility and existence as a solid-phase material minimizes any contamination to the treated solution caused by the recovery process. Further, these chelating resins are often suitable for removing metal ions from solutions too dilute for practicable liquid-liquid extractions.

One resin attribute of great interest has been selectivity for particular metal ions. Desirable chelating resins preferentially bind valuable metal ions (e.g. copper and nickel) over less valuable metals ions (e.g. iron) at acid pHs (e.g pHs of 1–4) which most often prevail in hydrometalurgical recovery operations. In this regard, certain resins incorporating alkylaminopyridyl, imidazolyl or pyridylimidazolyl functions have been reported to selectively bind these valuable metal ions.

For instance, U.S. Pat. No. 4,202,944 to Hancock et al. describes resins which incorporate pyridyl, imidazolyl or imidazoline groups. The described resins are prepared by treating a preformed chloromethylated polystyrene matrix with a solution containing the active species of interest. The active species are thereby attached to the chloromethylated polystyrene matrix. Similarly, U.S. Pat. No. 4,031,038 to Grinstead et al. describes chelate-exchange resins capable of selective recovery of copper, nickel, and other valuable metals from acidic aqueous leachate liquor. Again, the resins are prepared by subsequently treating preformed chloromethylated styrene-divinylbenzene copolymer beads, this time with an aminomethylpyridine species.

Resin preparations with chloromethylated polystyrene have been extensively reviewed. See, "Chemical Transformations of Chloromethylated Polystyrene", *J. Macromol. Sci. - Rev. Macromol. Chem. Phys.*, 28, 503–592 (1988); "Chloromethylstyrene: Synthesis, Polymerization, Transformations, Applications", *J. Macromol. Sci. - Rev. Macromol. Chem. Phys.*, 22, 343–407 (1982-83). As these reviews and the above-described patents demonstrate, by far, the predominant preparative approach in the literature and industry has been to react preformed chloromethylated polystyrene beads with a solution of the ligand of interest. In only relatively few instances, monomers incorporating the species of interest have been prepared and polymerized. This approach has seemingly been discarded in many instances, possibly due to difficulties encountered in preparing monomers of sufficient purity to give superior polymer products. For example, distillation, by far the most commonly used purifying method, has not been found to reliably purify monomers incorporating complicated ligands of interest. See, for instance, M. Tomoi, Y. Akada and H. Kakuichi, *Macromol. Chem., Rapid Commun.*, 3, 537–42 (1982). As such, the monomers will contain substantial impurities, as will the polymers derived from them. This can severely impact selectivity of the polymers.

While efforts in the art and industry have provided chelating resins demonstrating some selectivity for certain valuable metals, the primary preparative method has been attachment of ligands to preformed chloromethylated polymer beads. As the applicants' own experience has shown, however, polymers prepared in this fashion have several disadvantages. For instance, the ligand attachment reaction very often gives rise to undesirable byproduct ligands irreversibly attached to the resin which can diminish selectivity. In light of the foregoing, there remains a need and demand for highly selective chelating resins, and to monomers and methods for their preparation. It is this need to which the invention described herein is addressed.

SUMMARY OF THE INVENTION

Accordingly, this invention provides in one preferred embodiment a polymerizable monomer for preparing a selective chelating resin, having the general formula I or II:

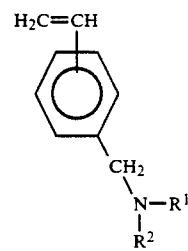

I

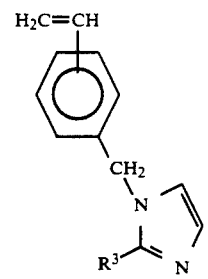

II wherein $R^1 = (CH_2)_n\text{-Py}$ where $n = 1$ to 3 and Py = a pyridyl group; $R^2 = H$, a $C_1$ to $C_{12}$ alkyl group or, independently, another group of the formula $R^1$; and $R^3 = $ a pyridyl group. These preferred polymerizable monomers have been prepared in substantially pure form, preferably free from decomposition products occurring from distillation, and have proven to be highly valuable materials enabling direct preparation of chelating resins having high selectivity for valuable metal ions in solution. Further, acid addition salts of the preferred monomers have proven to be unexpectedly stable and accordingly constitute another preferred embodiment of the invention.

Another preferred embodiment of this invention relates to a process for producing a chelating resin. This process comprises a polymerization including a preferred monomer as described above.

Another preferred embodiment of the invention includes a chelating resin having repeating units derived from a polymerizable monomer as described above.

These preferred embodiments provide highly valuable materials and processes demonstrating unexpected properties, and are or can be used to prepare extraordinarily selective metal chelating resins. Additional objects and advantages of the invention will become apparent upon reviewing the following description and appended claims.

DESCRIPTION OF THE PREFERRED EMBODIMENT

For the purposes of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As indicated above, one preferred embodiment of this invention relates to a polymerizable monomer for preparing a selective chelating resin. Generally, monomers of the invention include a vinylbenzyl moiety N-bonded to an alkylaminopyridyl function (e.g.—$(CH_2)_n$—Py of formula I) or a pyridylimidazolyl function (e.g. formula II).

As previously set forth, the preferred alkylaminopyridyl function $R^1$ (and optionally $R^2$) has the formula —$(CH_2)_n$—Py wherein $n=$an integer from 1 to 3, and Py is a pyridyl group, e.g. a 2-, 3- or 4-pyridyl group, more Preferably 2-pyridyl. Further, n is preferably 1 (i.e. a methylene group is provided). As such, more preferred monomers of the invention include N-vinylbenzyl-N-2-picolylamine derivatives, for instance N-vinylbenzyl-N-2-picolylamine itself (i.e. $R^1 =$—$CH_2$—Py where Py is 2-pyridyl, and $R^2 =$H). $R^2$ as stated, can, independently, be another group of the formula $R^1$. Especially preferred are monomers where $R^1$ and $R^2$ are identical, e.g. as in the case of N-vinylbenzyl-N-(bis)2-picolylamine. Additional preferred monomers result where $R^2$ is an alkyl group, preferably a $C_1$ to $C_{12}$ alkyl, which can be unsubstituted or substituted with groups that do not detrimentally interfere with polymerization or with selectivity of the final resin. For instance, the alkyl group can be a hydroxyalkyl group such as 2-hydroxyethyl or 2-hydroxypropyl. Accordingly, additional preferred monomers include N-vinylbenzyl-N-2-hydroxyethyl-N-2-picolylamine and N-vinylbenzyl-N-2-hydroxypropyl-N-2-picolylamine.

As stated, additional preferred monomers occur within formula II, i.e. where a pyridylimidazolyl function is included. In the preferred monomers these pyridylimidazolyl functions are N-bonded to the vinylbenzyl moiety at the 1 position of the imidazolyl ring. The pyridylimidazolyl function is desirably a 2-pyridylimidazolyl function, for example as occurs in the preferred monomer 1-vinylbenzyl-2-(2-pyridyl)imidazole.

As those skilled in the art will recognize and appreciate, the ring systems present in the preferred monomers can be substituted with additional noninterfering groups (e.g. alkyl, etc.) which do not detrimentally affect the function of the monomers or the polymers derived from them. Such modifications are contemplated as providing monomers and polymers of equivalent nature and function and are therefore within the spirit and scope of the present invention.

The preferred monomers can be prepared by first reacting a hydride, hydroxide or alkoxide salt, e.g. sodium hydride, potassium hydroxide or sodium ethoxide, with a compound of the formula $HNR^1R^2$ or $HNCHCHNC$-$R^3$ where $R^1$, $R^2$ and $R^3$ are as previously defined, to thereby form the corresponding $Na^+$ $^-NR^1R^2$ or $Na^+$ $^-\overline{NCHCHNC}$-$R^3$ salt. This salt is then reacted with vinylbenzyl chloride to form the desired monomer, which can then be conventionally filtered to remove inorganics, and concentrated. Also, where $R^2 =$H in the monomer product, this product can be further reacted with a functionalizing agent, e.g. an epoxy compound such as ethylene or propylene oxide, to thereby functionalize (e.g. hydroxyalkylate in the case of epoxides) at the $R^2$ position.

In a preferred preparative process and further inventive embodiment, the monomer, once formed, is treated with an acid sufficiently strong to form an acid salt of the monomer. This acid addition salt is then purified by extraction into an aqueous layer, and optionally washed with toluene to remove neutral water insoluble impurities. After purification, the monomer can be converted back to free base form immediately or after storage by treatment with a basic substance, e.g. aqueous ammonia, and is preferably extracted at least once with a polar organic solvent such as methylene chloride. The resulting monomer has superior purity and is free from decomposition products occurring from distillation.

The acid salt form monomer demonstrates surprising improved stability against polymerization, both in solution and when isolated as a solid material. For instance, as illustrated in Example 11, when stored under refrigeration in free base form, monomers of the invention form dark, tarry material and are greater than 50% lost over a period of about 2 months, and further have proven unusable for the preferred polymerization procedures. On the other hand, acid salts of the monomers stored over similar periods in their solid form are essentially 100% retained, and in solution are at least 75% retained. Importantly, when converted back to free base form, the monomers stored as acid salts yield material which can be successfully polymerized to form the preferred selective chelating resins. These acid salt form monomers thus can be reliably stored and also constitute a further preferred embodiment of the invention. As to specific acids which can be used to prepare the preferred acid salt-form monomers, these include for instance hydrochloric, sulfuric, hydrobromic, methanesulfonic, formic and phosphoric acid although others will be suitable as those skilled in the area will appreciate.

In preferred work to date, the inventive monomers have been suspension copolymerized with at least one comonomer to provide a suitable crosslinked polymer matrix. For instance, it has proven highly desirable to suspension copolymerize the inventive monomer with styrene and divinylbenzene comonomers. The organic phase for the polymerization desirably contains divinylbenzene, styrene, the inventive monomer and a suitable polymerization catalyst, e.g. Vazo 52 available from E. I. du Pont de Nemours & Co., Inc. of Wilmington, Del., U.S.A. The monomers are typically included in ratios of about 2 to 30 weight % divinylbenzene:5 to 45 weight % styrene:30 to 65 weight % inventive monomer. More desirably, the inventive monomer comprises at least 50 weight % of the monomers to be polymerized. The preferred aqueous phase has been a 0.2% solution of Methocel 50-123, a material commercially available from Dow Chemical Co. of Midland Mich., U.S.A., although other aqueous phases will of course be suitable and their utilization well within the purview of those practiced in the field.

The resulting resins can be gel or macroreticular form, preferably beads, and demonstrate superior selectivities and affinities for for copper and other valuable metal ions. The resins of the invention also have excellent iron rejection values and thus provide superior selective and cost-effective recovery of valuable metal ions in many applications.

As to recovering the copper or other metal from the resin, this can be conventionally accomplished by elution with a strong acid such as sulfuric or hydrochloric acid. The resins can then be used directly in another metal recovery, or optionally can be regenerated by treatment with an aqueous base (NaOH, $NH_3$, etc.) prior to use in a subsequent run. As another example, copper ions can also be selectively removed with aqueous ammonia.

For the purposes of promoting a further understanding of the invention the following examples are provided. It will be understood that these examples are illustrative and are not intended to be restrictive of the invention.

EXAMPLE 1

Preparation of N-Vinylbenzyl-N-(bis)2-picolylamine

Sodium hydride was initially washed with hexane to remove mineral oil. The hexane-wet solid contained 60% sodium hydride. Twenty-eight grams (0.694 mole) of the wet hydride were combined with 300 mL of anhydrous THF in a previously dried round bottom flask fitted with stirrer, thermometer, nitrogen inlet and a reflux condenser. Bis-2-picolylamine (112.6 g, 0.565 mole) was added and the resulting mixture stirred for three hours. During this time the reaction temperature rose to 40° C. and $H_2$ was evolved. After three hours the reaction temperature had returned to 25° C. and a solution containing 98.6 g of vinylbenzyl chloride (0.564 mole) in 75 mL of THF was added dropwise while the reaction temperature was maintained between 30–40° C. with cooling. When the addition of vinyl benzyl chloride solution was complete, the reaction mixture was stirred for 20 hours at room temperature under a nitrogen purge. The reaction mixture was then filtered and concentrated at reduced pressure to give 174 g of the N-vinylbenzyl-N-(bis)2-picolylamine monomer.

EXAMPLE 2

Preparation of N-Vinylbenzyl-N-(bis)2-picolylamine via Acid Salt

Bis-2-picolylamine (79.7 g, 0.4 mole), sodium hydride (80 wt. % in oil, 14.9 g, 0.5 mole), and anhydrous THF (250 mL) were combined with stirring in a dry, nitrogen-purged round bottom flask. Stirring was continued until no more heat or hydrogen were evolved and toluene (600 mL) was added. The majority of the THF was removed from the mixture by distillation and the reaction mixture cooled to room temperature. Commercial vinylbenzyl chloride (63.6 g) was added slowly and the reaction maintained below 40° C. for 6 hours. Unreacted sodium hydride was quenched with water and carbon dioxide and the reaction mixture filtered to remove sodium chloride.

With cooling, keeping the temperature below 40° C., 10 wt. % hydrochloric acid (115 mL) was added to the filtrate. The aqueous layer containing the monomer was separated, washed with toluene. The original toluene layer was washed with two 100 mL portions of water and all water layers combined. The pH of the aqueous solution was adjusted to 9.0 with aqueous ammonia. The monomer was extracted with three 100 mL portions of methylene chloride and the combined organic layers concentrated at reduced pressure to give 113.5 grams of the Bis-2-picolylamine monomer.

EXAMPLE 3

Further Preparation of N-Vinylbenzyl-N-(bis)2-picolylamine

Potassium hydroxide (85%, 29.4 g, 0.446 mole) and acetonitrile (200 mL) were combined and heated to reflux for 30 minutes. The mixture was cooled to room temperature and Bis-2-picolylamine (79,8 g, 0.4 mole) was added to give a purple solution that changed to brown. Vinylbenzylchloride (96%, 63.6 g, 0.4 mole) was added dropwise during fifteen minutes with stirring and cooling to hold the reaction temperature at 45° C. or less for 18 hours, solvent was removed at reduced pressure and the resulting residue dissolved in toluene (200 mL). The toluene solution was first washed with two portions of water (200 mL) and then extracted with aqueous acid (75 mL of concentrated HCl diluted with 200 mL of water). The acid layer was separated, treated with aqueous ammonia (100 mL) until basic, and extracted with methylene chloride (100 mL) and cyclohexane (200 mL). The extracts were combined, dried over anhydrous magnesium sulfate, and concentrated at reduced pressure to give 129.8 g of the title monomer containing less than 2% of unreacted Bis-2-picolylamine.

EXAMPLE 4

Preparation of N-Vinylbenzyl-N-2-picolylamine

The procedure described in Example 1 above was carried out with 43.3 g (0.4 mole) of 2-picolylamine substituted for the bis-2-picolylamine. Concentration of the methylene chloride gave 82.5 g of the N-vinylbenzyl-N-2-picolylamine monomer.

EXAMPLE 5

Preparation of 1-Vinylbenzyl-2-(2-pyridyl)imidazole

Step (a) - preparation of 2-(2-pyridyl)imidazole: Generally, the procedure described in U. S. Pat. No. 4,202,944 was used to prepare 2-(2-pyridyl)-imidazole. Accordingly, with stirring and cooling, chilled solutions containing 14.9 g of 2-pyridylaldehyde in 14.5 mL of ethanol and 30 mL of 30% aqueous glyoxal solution in 15 mL of ethanol were combined. Immediately and with continued cooling, 40 mL of cold 2.0 N aqueous ammonia were added. The reaction mixture was stirred for 1 hour at 0 to 2° C. and then at room temperature for 17 hours. Solvent was removed at reduced pressure and the residue extracted with 5×30 mL portions of diethyl ether. The ether extracts were combined and after establishing the absence of peroxides, concentrated and distilled to give 9.7 g of 2-(2-pyridylimidazole) as an oil that solidified upon cooling.

Step (b)—reaction with vinylbenzyl chloride—Using the procedure in Example 1, 82.0 g (0.567 mole) of 2-(2-pyridylimidazole) were reacted with 99.1 g (0.567 mole) of vinylbenzyl chloride to give 141.0 g of the pyridylimidazole monomer. The reaction can also be carried out using sodium ethoxide instead of sodium hydride.

EXAMPLE 6

Preparation of N-Vinylbenzyl-N-2-picolyl-N-2-hydroxyethylamine

To a stirred solution containing 134.6 g (0.6 mole) of the 2-picolylamine substituted monomer of Example 4 in 300 mL of tetrahydrofuran were added dropwise 27.3 g (0.62 mole) of ethylene oxide over a 2 hour period. The reaction mixture was allowed to stir at room temperature for 20 hours and the solvent removed at reduced pressure to give 153.0 g of the hydroxyethylamine substituted monomer. This procedure is repeated, except substituting propylene oxide for the ethylene oxide, to provide the corresponding hydroxypropylamine substituted monomer.

EXAMPLE 7

Preparation of Aqueous and Organic Phases for Polymerization

A 1.7% solution of METHOCEL 50- 123 was prepared according to the manufacturer's instructions by dispersing the solid in water, with vigorous stirring, at about 85° C. and then adding ice to rapidly cool the mixture. For the reactions described below, this solution was diluted to give a 0.17% solution of METHOCEL 50-123. Organic phases were prepared containing 55% divinylbenzene, styrene, and amine substituted monomer, and a catalyst, Vazo 52.

EXAMPLE 8

Polymerization Including N-Vinylbenzyl-N-2-picolylamine

One hundred and sixty milliliters of the 0.17% METHOCEL 50-123 were heated to 55° C under a nitrogen purge in a round-bottom flask fitted with a thermometer and stirrer. A monomer solution containing 1.2 g of 55% divinylbenzene, 6.9 g of styrene, 9.96 g of the monomer prepared in Example 4, and 0.1 g of Vazo 52 was added to the stirred aqueous solution in one portion below the liquid level. The reaction temperature was maintained at 55° C. for 3 hours and then increased to 80° C. where it was held for 18 hours. The resulting slurry was cooled, and the product orange beads were filtered and rinsed with water and methanol, and dried.

EXAMPLE 9

Polymerization Including N-Vinylbenzyl-N-(bis)2-picolylamine

The procedure of Example 8 was used to polymerize a mixture containing 1.2 grams of 55% divinylbenzene, 6.9 grams of styrene, 14.05 grams of the monomer of Example 2, and 0.1 g of Vazo 52. A light tan polymer resulted.

EXAMPLE 10

Polymerization Including 1-Vinylbenzyl-2-(2-pyridyl)imidazole

The polymerization method described in Example 8 above was used to polymerize an organic mixture containing 1.2 g of 55% divinylbenzene, 6.9 g of styrene, 11.3 g of the monomer prepared in Example 5, and 0.1 g of Vazo 52. Hard, light yellow beads of uniform size were obtained.

EXAMPLE 11

Stability of Free Base Monomers vs. Acid Salt Counterparts

The monomer preparation described in Example 2 was repeated with the following changes. After reaction of the sodium hydride adduct of bis-2-picolylamine with vinylbenzyl chloride, a majority of the THF was removed as before and the reaction mixture cooled. The unreacted sodium hydride was quenched with carbon dioxide and a minimum of water and the mixture filtered as before to remove sodium chloride. The toluene solution was divided into three equal portions, and each portion was worked up as described below.

Portion 1: A first portion of the toluene solution was concentrated at reduced pressure over several hours while keeping the liquid temperature below 55° C., and the resulting dark oil stored in a refrigerator for 61 days. During this time, the oil darkened and became more viscous GC analysis (OV 1701, 80° C., 0 hold time, 16° C./min. to 280° C.) indicated loss of more than 60% of the monomer. The major decomposition product appeared to be polymeric. Attempts to polymerize the monomer as described in Example 8 were discontinued when large amounts of tarry material precipitated upon adding the divinylbenzene and styrene monomers to the dark viscous oil.

Portion 2: A second portion of the toluene solution was dried over anhydrous sodium sulfate, after which anhydrous hydrochloric acid was added through a bubbler to the stirred and cooled solution. The white solid (the hydrochloride salt of N-vinylbenzyl-N-(bis)2-picolylamine) that formed was filtered, washed with fresh toluene and air dried at room temperature. The white solid was stored for 61 days at room temperature without any visible changes in appearance or its infrared spectrum. The acid salt of the monomer was dissolved in water, treated with aqueous base, and extracted as in Example 2 to give the monomer in its free base form. Polymerization as described in Example 9 gave the expected polymer.

Portion 3: A third portion of the toluene solution was extracted with two portions of 5% aqueous hydrochloric acid and the acidic layers containing the acid salt of N-vinylbenzyl-N-(bis)2-picolylamine were combined and stored in a refrigerator. At the end of 64 days, the aqueous layer was decanted from some tarry material that had formed, made basic with aqueous sodium hydroxide, and extracted with three portions of toluene. The organic layers were combined and concentrated at reduced pressure over several hours while keeping the liquid temperature below 55° C. GC analysis (OV only 1701, 80° C., 0 hold time, 16° C./min. to 280° C.) indicated loss of about 25% of the monomer. The major decomposition product appeared to be the tarry polymeric material formed in the aqueous solution of the acid salt. The monomer isolated was polymerized as described in Example 9 to give the desired polymer.

Similar surprising and improved stability was observed for the acid salts of N-vinylbenzyl-N-2-picolylamine and N-vinylbenzyl-N-2-(2-pyridylimidazoline).

What is claimed is:

1. A substantially pure polymerizable monomer for preparing a selective chelating resin, having the general formula:

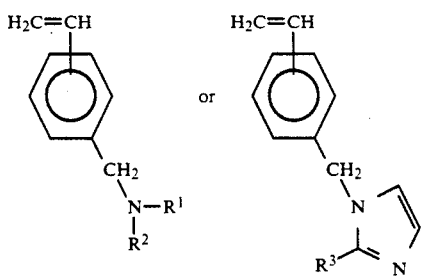

wherein
$R^1 = (CH_2)_n$ - Py wherein $n = 1$ to 3 and Py = a pyridyl group;
$R^2 =$ H, a $C_1$ to $C_{12}$ alkyl group optionally a hydroxyalkyl group or, independently, another group of the formula $R^1$; and
$R^3 =$ a pyridyl group.

2. A polymerizable monomer according to claim 1 which has the general formula

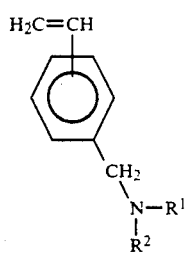

wherein $R^1 = (CH_2)_n$ - Py wherein $n = 1$ to 3 and Py = a pyridyl group; and
$R^2 =$ H, a $C_1$ to $C_{12}$ alkyl group, hydroxyalkyl group or,
independently, another group of the formula $R^1$.

3. A polymerizable monomer according to claim 2, wherein $R^2 =$ H.

4. A polymerizable monomer according to claim 2 wherein
$R^2 =$ a $C_1$ to $C_{12}$ alkyl group or hydroxyalkyl group.

5. A polymerizable monomer according to claim 2 wherein
$R^2$ is, independently, another group of the formula $R^1$.

6. A polymerizable monomer according to claim 2, wherein
$n = 1$ and Py = a 2-pyridyl group.

7. A polymerizable monomer according to claim 6, wherein
$R^2 =$ H.

8. A polymerizable monomer according to claim 6, wherein
$R^2 =$ a $C_1$ to $C_{12}$ alkyl group or a hydroxyalkyl group 9. A polymerizable monomer according to claim 8, wherein $R^2$ is a hydroxyalkyl group.

10. A polymerizable monomer according to claim 9, wherein said hydroxyalkyl group is a hydroxyethyl or hydroxypropyl group.

11. A polymerizable monomer according to claim 10, wherein said hydroxyalkyl group is a hydroxyethyl group.

12. A polymerizable monomer according to claim 11, wherein said hydroxyethyl group is a 2-hydroxyethyl group.

13. A polymerizable monomer according to claim 10, wherein said hydroxyalkyl group is a hydroxypropyl group., 14. A polymerizable monomer according to claim 13, wherein said hydroxypropyl group is a 2-hydroxypropyl group.

15. A polymerizable monomer according to claim 6, wherein $R^2$ is, independently, another group of the formula $R^1$.

16. A polymerizable monomer according to claim 15, wherein $n = 1$ in each of $R^1$ and $R^2$.

17. A polymerizable monomer according to claim 16, wherein Py is a 2-pyridyl group in each of $R^1$ and $R^2$.

18. A polymerizable monomer according to claim 1, which has the general formula

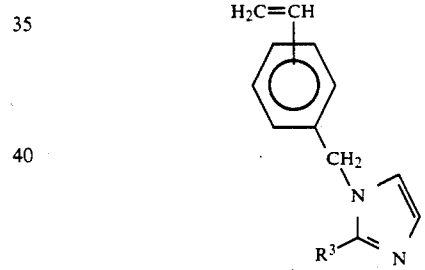

wherein $R^3 =$ a pyridyl group.

19. A polymerizable monomer according to claim 18, wherein $R^3 =$ a 2-pyridyl group.

20. As a composition of matter, a polymerizable monomer according to claim 1 isolated as an acid salt.

21. A composition of claim 20 which is an acid salt of a polymerizable monomer selected from the group consisting of
N-vinylbenzyl-N-(bis)2-picolylamine;
N-vinylbenzyl-N-2-picolylamine;
1-vinylbenzyl-2-(2-pyridyl)imidazole;
N-vinylbenzyl-N-2-hydroxyethyl-N-2-picolylamine; and
N-vinylbenzyl-N-2-hydroxypropyl-N-2-picolylamine.

22. A composition of claim 21, which is an acid salt of N-vinylbenzyl-N-(bis)2-picolylamine.

* * * * *